(12) United States Patent
Anderson

(10) Patent No.: US 9,402,981 B2
(45) Date of Patent: Aug. 2, 2016

(54) SUBINTIMAL RE-ENTRY CATHETER AND RETROGRADE RECANALIZATION

(71) Applicant: Boston Scientific Scimed, Inc., Maple Grove, MN (US)

(72) Inventor: James M. Anderson, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 637 days.

(21) Appl. No.: 13/622,128

(22) Filed: Sep. 18, 2012

(65) Prior Publication Data

US 2013/0072957 A1  Mar. 21, 2013

Related U.S. Application Data

(60) Provisional application No. 61/536,229, filed on Sep. 19, 2011.

(51) Int. Cl.
| | |
|---|---|
| *A61M 29/00* | (2006.01) |
| *A61M 25/10* | (2013.01) |
| *A61M 25/01* | (2006.01) |
| *A61B 17/3207* | (2006.01) |
| *A61M 25/00* | (2006.01) |
| *A61B 17/00* | (2006.01) |
| *A61B 17/22* | (2006.01) |

(52) U.S. Cl.
CPC .......... *A61M 25/104* (2013.01); *A61B 17/3207* (2013.01); *A61B 17/320758* (2013.01); *A61B 2017/00331* (2013.01); *A61B 2017/22061* (2013.01); *A61B 2017/22071* (2013.01); *A61B 2017/22095* (2013.01); *A61B 2017/320733* (2013.01); *A61M 25/0194* (2013.01); *A61M 2025/0096* (2013.01); *A61M 2025/018* (2013.01); *A61M 2025/0197* (2013.01); *A61M 2025/1043* (2013.01)

(58) Field of Classification Search
CPC .................. A61B 17/3207; A61B 2017/22095; A61B 2017/320733; A61M 25/0194; A61M 25/104; A61M 2025/018; A61M 2025/1043
See application file for complete search history.

(56) References Cited

U.S. PATENT DOCUMENTS

| | | | | |
|---|---|---|---|---|
| 4,878,495 | A | * | 11/1989 | Grayzel ................ A61M 29/02 604/101.01 |
| 5,690,642 | A | | 11/1997 | Osborne et al. |
| 5,814,061 | A | | 9/1998 | Osborne et al. |
| 5,830,222 | A | | 11/1998 | Makower et al. |
| 5,935,108 | A | | 8/1999 | Katoh et al. |

(Continued)

FOREIGN PATENT DOCUMENTS

| | | |
|---|---|---|
| WO | 9744083 A1 | 11/1997 |
| WO | 2009100129 A2 | 8/2009 |

(Continued)

*Primary Examiner* — Robert Lynch
(74) *Attorney, Agent, or Firm* — Seager, Tufte & Wickhem LLP

(57) ABSTRACT

A catheter for recanalizing a blood vessel having an occlusion therein via a subintimal pathway. The catheter includes a catheter shaft having an inflatable balloon mounted to the distal end portion of the catheter shaft. A flexible tubular member extends from the catheter shaft and along an exterior of the inflatable balloon. Inflation of the inflatable balloon deflects the flexible tubular member into a deflected configuration away from a longitudinal axis of the catheter shaft to effect re-entry into the true lumen distal of the occlusion.

16 Claims, 15 Drawing Sheets

(56) References Cited

U.S. PATENT DOCUMENTS

| | | | |
|---|---|---|---|
| 5,938,671 A | 8/1999 | Katoh et al. | |
| 5,968,064 A | 10/1999 | Selmon et al. | |
| 6,010,449 A | 1/2000 | Selmon et al. | |
| 6,068,638 A | 5/2000 | Makower et al. | |
| 6,120,516 A | 9/2000 | Selmon et al. | |
| 6,159,225 A | 12/2000 | Makower et al. | |
| 6,190,353 B1 | 2/2001 | Makower et al. | |
| 6,217,527 B1 | 4/2001 | Selmon et al. | |
| 6,217,549 B1 | 4/2001 | Selmon et al. | |
| 6,221,049 B1 | 4/2001 | Selmon et al. | |
| 6,231,546 B1 | 5/2001 | Milo et al. | |
| 6,231,587 B1 | 5/2001 | Makower | |
| 6,235,000 B1 | 5/2001 | Milo et al. | |
| 6,241,667 B1 | 6/2001 | Vetter et al. | |
| 6,371,961 B1 | 4/2002 | Osborne et al. | |
| 6,398,798 B2 | 6/2002 | Selmon et al. | |
| 6,475,226 B1 * | 11/2002 | Belef et al. | 606/185 |
| 6,506,178 B1 | 1/2003 | Schubart et al. | |
| 6,508,825 B1 | 1/2003 | Selmon et al. | |
| 6,511,458 B2 | 1/2003 | Milo et al. | |
| 6,514,217 B1 | 2/2003 | Selmon et al. | |
| 6,579,302 B2 | 6/2003 | Duerig et al. | |
| 6,599,304 B1 | 7/2003 | Selmon et al. | |
| 6,638,247 B1 | 10/2003 | Selmon et al. | |
| 6,663,577 B2 | 12/2003 | Jen et al. | |
| 6,719,725 B2 | 4/2004 | Milo et al. | |
| 6,955,175 B2 | 10/2005 | Stevens et al. | |
| 7,004,173 B2 | 2/2006 | Sparks et al. | |
| 7,008,438 B2 * | 3/2006 | O'Brien | A61M 25/04 604/103.08 |
| 7,179,270 B2 | 2/2007 | Makower | |
| 7,229,421 B2 | 6/2007 | Jen et al. | |
| 7,357,794 B2 | 4/2008 | Makower et al. | |
| 7,740,623 B2 | 6/2010 | Nayak et al. | |
| 7,771,462 B1 | 8/2010 | Davidson et al. | |
| 7,918,859 B2 | 4/2011 | Katoh et al. | |
| 7,918,870 B2 | 4/2011 | Kugler et al. | |
| 7,938,819 B2 | 5/2011 | Kugler et al. | |
| 8,025,655 B2 | 9/2011 | Kugler et al. | |
| 8,083,727 B2 | 12/2011 | Kugler et al. | |
| 8,172,863 B2 | 5/2012 | Robinson et al. | |
| 8,202,246 B2 | 6/2012 | Kugler et al. | |
| 2001/0000041 A1 | 3/2001 | Selmon et al. | |
| 2001/0012924 A1 | 8/2001 | Milo et al. | |
| 2002/0103459 A1 | 8/2002 | Sparks et al. | |
| 2002/0128677 A1 | 9/2002 | Duerig et al. | |
| 2003/0120195 A1 | 6/2003 | Milo et al. | |
| 2003/0139763 A1 | 7/2003 | Duerig et al. | |
| 2005/0171478 A1 | 8/2005 | Selmon et al. | |
| 2006/0094930 A1 | 5/2006 | Sparks et al. | |
| 2006/0167554 A1 | 7/2006 | Heck et al. | |
| 2006/0184011 A1 | 8/2006 | Macaulay et al. | |
| 2006/0230219 A1 | 10/2006 | Njoku et al. | |
| 2006/0276749 A1 | 12/2006 | Selmon et al. | |
| 2007/0093779 A1 | 4/2007 | Kugler et al. | |
| 2007/0093780 A1 | 4/2007 | Kugler et al. | |
| 2007/0093781 A1 | 4/2007 | Kugler et al. | |
| 2007/0093782 A1 | 4/2007 | Kugler et al. | |
| 2007/0219464 A1 * | 9/2007 | Davis et al. | 600/585 |
| 2007/0265596 A1 | 11/2007 | Jen et al. | |
| 2008/0033423 A1 | 2/2008 | Peacock | |
| 2008/0125748 A1 | 5/2008 | Patel | |
| 2008/0154172 A1 | 6/2008 | Mauch | |
| 2008/0200896 A1 | 8/2008 | Shmulewitz et al. | |
| 2008/0228171 A1 | 9/2008 | Kugler et al. | |
| 2008/0243065 A1 | 10/2008 | Rottenberg et al. | |
| 2008/0243067 A1 | 10/2008 | Rottenberg et al. | |
| 2008/0249397 A1 | 10/2008 | Kapadia | |
| 2008/0306499 A1 | 12/2008 | Katoh et al. | |
| 2009/0005755 A1 | 1/2009 | Keith et al. | |
| 2009/0088685 A1 | 4/2009 | Kugler et al. | |
| 2009/0093791 A1 | 4/2009 | Heuser | |
| 2009/0124899 A1 | 5/2009 | Jacobs et al. | |
| 2009/0209910 A1 * | 8/2009 | Kugler | A61B 17/11 604/103.1 |
| 2009/0264826 A1 | 10/2009 | Thompson | |
| 2009/0292296 A1 | 11/2009 | Pansky et al. | |
| 2009/0299171 A1 | 12/2009 | Duffy et al. | |
| 2009/0299402 A1 | 12/2009 | Orihashi et al. | |
| 2010/0063534 A1 | 3/2010 | Kugler et al. | |
| 2010/0067745 A1 | 3/2010 | Kovtun et al. | |
| 2010/0069945 A1 | 3/2010 | Olson et al. | |
| 2010/0125244 A1 | 5/2010 | McAndrew | |
| 2010/0317973 A1 | 12/2010 | Nita | |
| 2011/0112564 A1 | 5/2011 | Wolf | |
| 2011/0144677 A1 | 6/2011 | Ward et al. | |
| 2011/0144742 A1 * | 6/2011 | Madrid | A61F 2/2433 623/2.11 |
| 2013/0006167 A1 | 1/2013 | Alvarez et al. | |
| 2013/0006173 A1 | 1/2013 | Alvarez et al. | |
| 2014/0371718 A1 | 12/2014 | Alvarez et al. | |

FOREIGN PATENT DOCUMENTS

| | | |
|---|---|---|
| WO | 2011025855 A2 | 3/2011 |
| WO | 2013036419 A1 | 3/2013 |

* cited by examiner

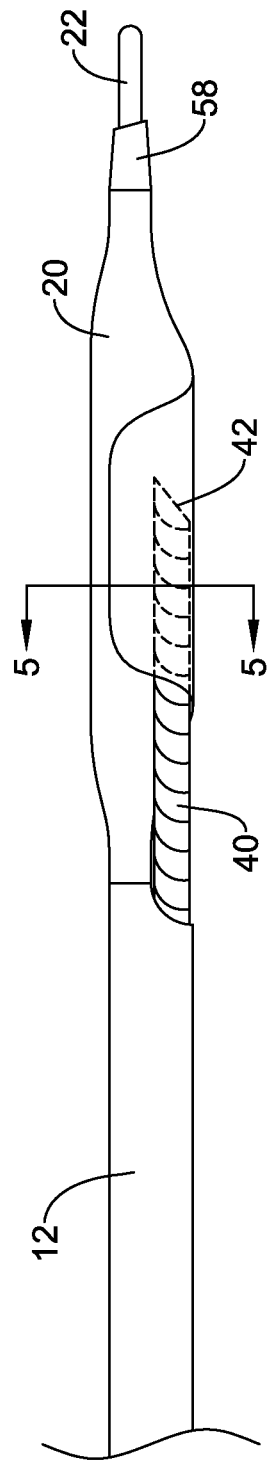
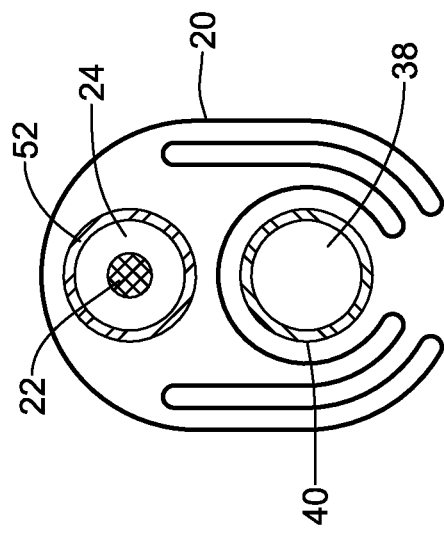
Figure 4
Figure 5

SUBINTIMAL RE-ENTRY CATHETER AND RETROGRADE RECANALIZATION

CROSS-REFERENCE TO RELATED APPLICATIONS

This application claims priority to U.S. Provisional Application No. 61/536,229, filed on Sep. 19, 2011, the entire disclosure of which is incorporated herein by reference.

TECHNICAL FIELD

The disclosure is directed to devices and methods for recanalization of an occluded blood vessel. More particularly, the disclosure is directed to devices and methods for re-entry into the true lumen from the extraluminal or subintimal space of a blood vessel.

BACKGROUND

Chronic total occlusion (CTO) is an arterial vessel blockage that obstructs blood flow through the vessel, and can occur in both coronary and peripheral arteries. In some instances, it may be difficult or impossible to pass through the CTO with a medical device in an antegrade direction to recanalize the vessel. Accordingly, techniques have been developed for creating a subintimal pathway (i.e., a pathway between the intimal and adventitial tissue layers of the vessel) around the occlusion and then re-entering the true lumen of the vessel distal of the occlusion in an attempt to recanalize the vessel. In some instances re-entering the true lumen from the subintimal space and/or recanalization can be difficult. Accordingly, it is desirable to provide alternative recanalization devices and/or methods of recanalizing a blood vessel in which a CTO is present.

SUMMARY

The disclosure is directed to several alternative designs, materials and methods of manufacturing medical device structures and assemblies, and uses thereof.

Accordingly, one illustrative embodiment is a catheter for recanalizing a blood vessel having an occlusion therein. The catheter includes a catheter shaft having a proximal end, a distal end, and a distal end portion proximate the distal end. The catheter also includes an expandable member coupled to the distal end portion of the catheter shaft. A flexible tubular configuration away from a longitudinal axis of the catheter shaft.

Another illustrative embodiment is a catheter assembly for navigating through a lumen of a blood vessel to an occlusion in an antegrade direction that is configured to redirect an atherectomy device toward the occlusion in a retrograde direction in the lumen of the blood vessel. The catheter assembly includes a catheter shaft having a proximal end, a distal end and a distal end portion proximate the distal end. The catheter assembly also includes an inflatable balloon secured to the distal end portion of the catheter shaft. A tubular member extends distally from a location on the catheter shaft proximal of the inflatable balloon. The tubular member is configured to be deflectable away from the catheter shaft into a curved configuration upon inflation of the inflatable balloon.

Another illustrative embodiment is a method of recanalizing a blood vessel having an occlusion therein. The method includes advancing a catheter through a lumen of a blood vessel to a location proximal of a proximal end of an occlusion. A distal end of the catheter is directed between a first tissue layer and a second tissue layer of a wall of the vessel to a location distal of a distal end of the occlusion. Thereafter, a flexible tubular member of the catheter re-enters the lumen of the blood vessel distal of the distal end of the occlusion and an occlusion crossing device is delivered through a lumen of the flexible tubular member to the distal end of the occlusion. The occlusion crossing device is then advanced into the occlusion from the distal end of the occlusion toward the proximal end of the occlusion.

Yet another illustrative embodiment is a method of recanalizing a blood vessel having an occlusion therein. The method includes advancing a catheter through a lumen of a blood vessel to a location proximal of a proximal end of an occlusion. The catheter includes a balloon mounted thereon and a flexible tubular member extending along an exterior of the balloon. The distal end of the catheter is directed between a first tissue layer and a second tissue layer of a wall of the vessel to a location distal of a distal end of the occlusion. The balloon is inflated between the first tissue layer and the second tissue layer distal of the distal end of the occlusion, thereby deflecting the flexible tubular member into a deflected configuration. Thereafter, the flexible tubular member of the catheter re-enters the lumen of the blood vessel distal of the distal end of the occlusion with the flexible tubular member of the catheter in the deflected configuration.

The above summary of some example embodiments is not intended to describe each disclosed embodiment or every implementation of the aspects of the disclosure.

BRIEF DESCRIPTION OF THE DRAWINGS

The aspects of the disclosure may be more completely understood in consideration of the following detailed description of various embodiments in connection with the accompanying drawings, in which:

FIG. 4 is a side plan view of the distal portion of the catheter apparatus of FIG. 1 in a delivery configuration;

FIG. 5 is a cross-sectional view of the catheter apparatus of FIG. 4 taken along line 5-5;

Figure 1:
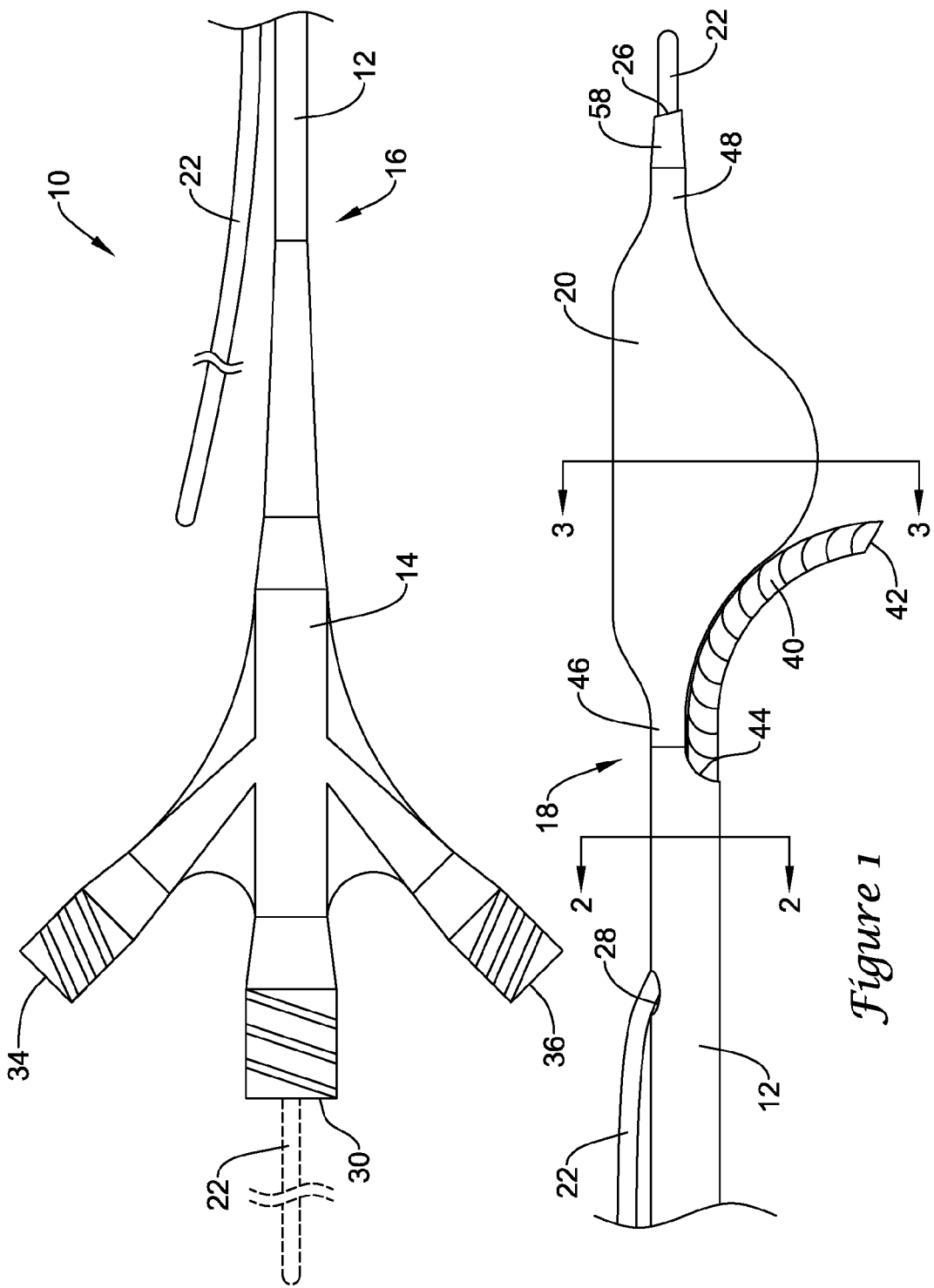
FIG. 1 is a side plan view of an exemplary catheter apparatus for recanalization of a blood vessel.

While the aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (i.e., having the same function or result). In many instances, the term "about" may be indicative as including numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

Although some suitable dimensions, ranges and/or values pertaining to various components, features and/or specifications are disclosed, one of skill in the art, incited by the present disclosure, would understand desired dimensions, ranges and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The detailed description and the drawings, which are not necessarily to scale, depict illustrative embodiments and are not intended to limit the scope of the disclosure. The illustrative embodiments depicted are intended only as exemplary. Selected features of any illustrative embodiment may be incorporated into an additional embodiment unless clearly stated to the contrary.

An exemplary recanalization catheter 10 is illustrated at FIG. 1. The recanalization catheter 10 may include a main catheter shaft 12 extending from a hub assembly 14 at a proximal end 16 of the catheter shaft 12 to an expandable member, shown as an inflatable balloon 20 mounted on a distal portion of the catheter shaft 12 proximate the distal end 18 of the catheter shaft 12. Although the expandable member is illustrated as an inflatable balloon 20, in some embodiments the expandable member may be an expandable framework formed of one or more, or a plurality of struts which may be automatically or manually expanded, or other manually expandable or automatically expandable structure.

The catheter 10 may be configured to be advanced over a guidewire 22 for delivery to a remote location in the vasculature of a patient. For example, in some instances the catheter 10 may be configured as a single-operator-exchange (SOE) catheter having a guidewire lumen 24 extending from a distal port 26 to a proximal guidewire port 28 located a short distance proximal of the balloon 20 and distal of the hub assembly 14. In such a configuration, the guidewire 22 may extend through the guidewire lumen 24 between the distal port 26 and the proximal port 28, and extend along an exterior of the catheter shaft 12 proximal of the proximal port 28 to the proximal end 16 of the catheter shaft 12. In other instances, the catheter 10 may be configured as an over-the-wire (OTW) catheter having a guidewire lumen 24 extending through the entire length of the catheter 10 from a distal port 26 at a distal tip of the catheter 10 to a proximal guidewire port 30 in the hub assembly 14. FIG. 1 illustrates such a configuration with the proximally extending portion of the guidewire 22 in dashed lines. It is noted that in instances in which the catheter 10 is an SOE catheter, the hub assembly 14 may not include a proximal guidewire port 30 and/or in instances in which the catheter 10 is an OTW catheter, the proximal guidewire port 28 may not be present.

The catheter shaft 12 may also include an inflation lumen 32 extending from an inflation port 34 of the hub assembly 14 to an interior of the balloon 20. The inflation lumen 32 may be configured for delivering inflation fluid to the balloon 20 to inflate the balloon 20 during a medical procedure.

The catheter 10 may also include a flexible tubular member 40 extending from the main catheter shaft 12 through opening 44. For example, in some instances the opening 44 may be a side opening extending through a sidewall of a tubular member of the main catheter shaft 12, or the opening 44 may be a distal opening at the distal end of a tubular member of the main catheter shaft 12. The flexible tubular member 40 may extend along a portion of the exterior of the balloon 20, such that an exterior surface of the balloon 20 may engage the flexible tubular member 40 when the balloon 20 is inflated. The flexible tubular member 40 may extend from the main catheter shaft 12 at a location proximal of the balloon 20, and extend distally therefrom, such that the flexible tubular member 40 extends exterior of the proximal waist 46 of the balloon 20, which may be secured to a portion of the main catheter shaft 12. In some instances, the distal tip 42 of the flexible tubular member 40 may terminate proximal of the distal waist 48 of the balloon 20, which may be secured to a portion of the main catheter shaft 12.

The flexible tubular member 40, which may be considered a deflectable re-entry tube or redirection tube (e.g., a "stinger") in some instances, may include flexibility characteristics permitting the flexible tubular member 40 to be deflected away from the main catheter shaft 12 (e.g., away from the central longitudinal axis of the main catheter shaft 12) into a curved or deflected configuration. In some instances, the flexible tubular member 40 may include one or more, or a plurality of cuts or slits formed through the sidewall of the flexible tubular member 40, providing the flexible tubular member 40 with a degree of lateral flexibility. For example, the flexible tubular member 40 may include a helical cut or slit formed through the sidewall of the flexible tubular member 40 and extending along a length of the flexible tubular member 40, an arrangement of a plurality of cuts or slits formed through the sidewall of the flexible tubular member 40 and extending partially around the circumference of the flexible tubular member 40 along a length of the flexible tubular member 40, or another arrangement of cuts or slits formed in another fashion to provide a desired degree of lateral flexibility.

In some embodiments, the flexible tubular member 40 may be formed of a metallic material, including a stainless steel or a nickel-titanium alloy such as nitinol, a polymeric material such as polyamide, polyether block amide, polyethylene, or polyethylene terephthalate, or a combination of metallic and polymeric materials, for example.

The flexible tubular member 40 may define a third, device delivery lumen 38 configured for delivering an elongated medical device to a target location via the catheter 10. The device delivery lumen 38 may extend from an access port 36 in the hub assembly 14 through the main catheter shaft 12 to the distal tip 42 of the flexible tubular member 40. Accordingly an elongated medical device may be inserted through the device delivery lumen 38 to be advanced from the distal tip 42 of the flexible tubular member 40 during a medical procedure.

Figure 2B:
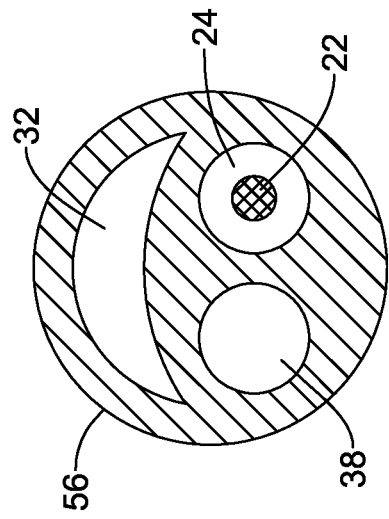
FIG. 2B is an alternative cross-sectional view of the catheter shaft of FIG. 1 taken along line 2-2.
Figure 2A:
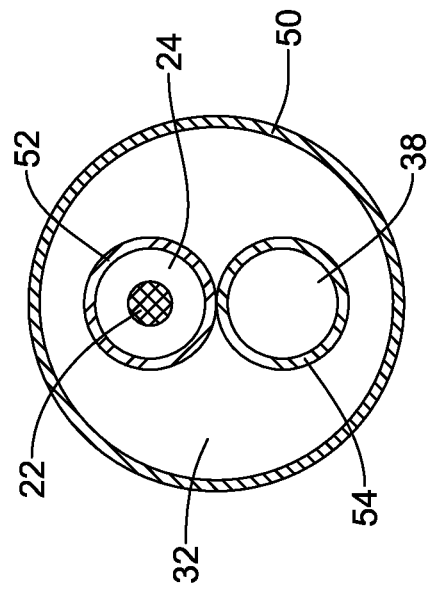
FIG. 2A is an exemplary cross-sectional view of the catheter shaft of FIG. 1 taken along line 2-2.

In some embodiments, as shown in FIG. 2A, the catheter shaft 12, or a portion thereof, may include an outer tubular member 50, a first inner tubular member 52 extending through the outer tubular member 50, and a second inner tubular member 54 extending through the outer tubular member 50. The first inner tubular member 52 may define the guidewire lumen 24, and the second inner tubular member 54 may define the device delivery lumen 38. The second inner tubular member 54 may be an extension of the flexible tubular member 40 extending into the outer tubular member 50, or the second tubular member 54 may be secured to the flexible tubular member 40 and extend therefrom, providing the device delivery lumen 38 therein. In such embodiments, the main catheter shaft 12 may be configured such that the proximal waist 46 of the balloon 20 is secured to the distal end of the outer tubular member 50, while the distal waist 48 of the balloon 20 is secured to the distal end of the first inner tubular member 52, extending through the interior of the balloon 20. Furthermore, the inflation lumen 32 may be defined between the outer tubular member 50 and the first and second inner tubular members 52, 54.

In other embodiments, as shown in FIG. 2B, the catheter shaft 12, or a portion thereof, may be an extruded shaft 56 having a plurality of lumens formed therein. For example, the extruded shaft 56 may include the guidewire lumen 24, the inflation lumen 32, and the device delivery lumen 38. In such embodiments, the main catheter shaft 12 may be configured such that the proximal waist 46 of the balloon 20 is secured to a portion of the extruded shaft 56, while the distal waist 48 of the balloon 20 is secured to another portion of the extruded shaft 56 or a tubular member extending therefrom, extending through the interior of the balloon 20.

The catheter 10 may also include a distal tip 58 extending distally from the balloon 20. The distal tip 58 may have a lumen extending therethrough and opening out to the distal port 26 at the distal end thereof to accommodate the guidewire 22 extending from the distal port 26. In some instances, the distal tip 58 may be an atraumatic tip, such as a flexible, low durometer tip similar to tips provided with typical angioplasty balloon catheters. However, in other embodiments, the distal tip 58 may be configured to facilitate piercing and/or dissection of tissue layers of the blood vessel. For example, the distal tip 58 may include a sharp, rigid and/or piercing feature. In one embodiment, as shown in FIG. 1, the distal tip 58 may include an angled distal edge, providing the distal tip 58 with a sharpened cutting or piercing edge.

Figure 3:
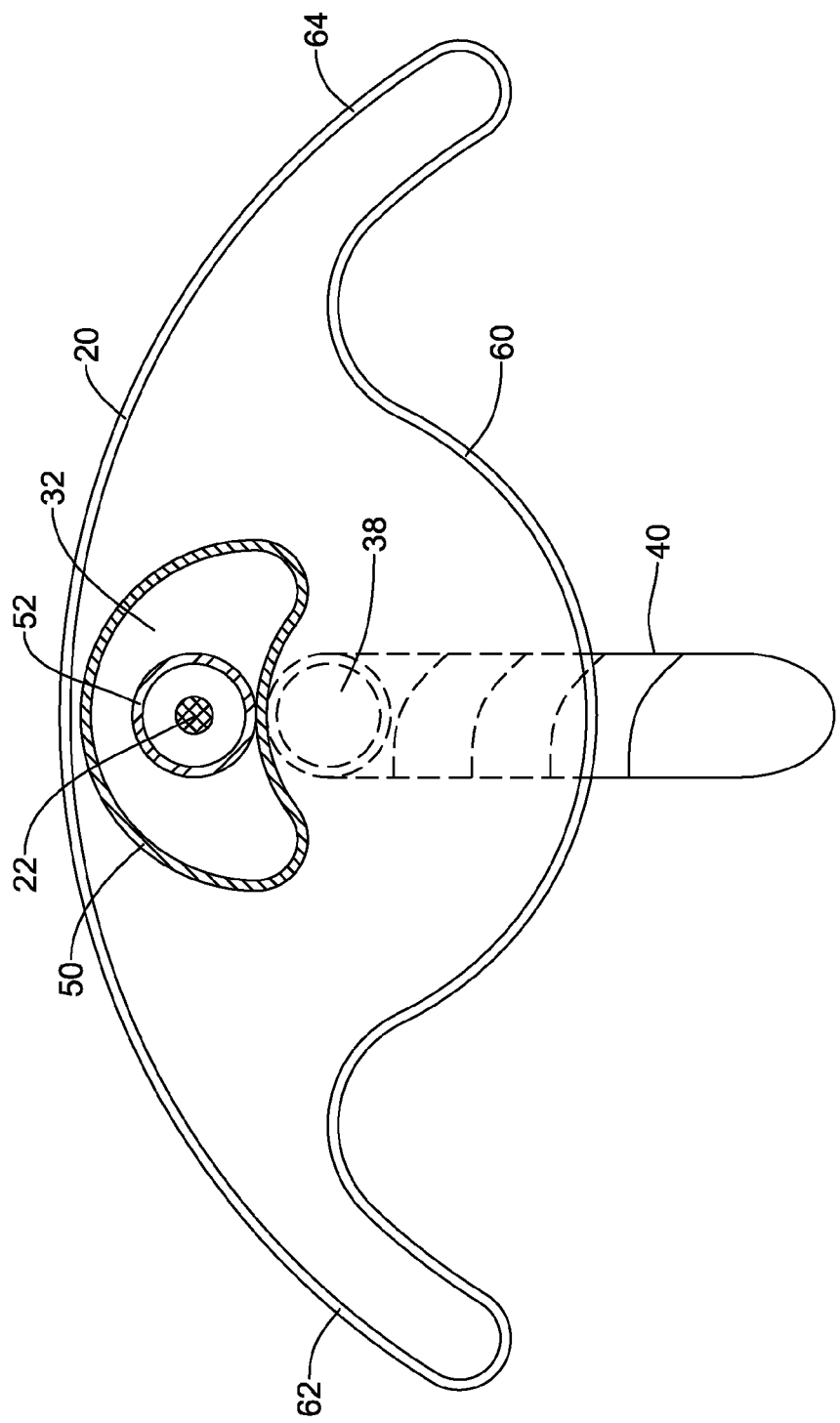
FIG. 3 is a cross-sectional view of the catheter apparatus of FIG. 1 taken along line 3-3.

FIG. 3 is a cross-sectional view of the catheter 10 taken through the balloon 20. As shown in FIG. 3, when inflated, the balloon 20 may include a central bulbous portion 60, a first wing portion 62 extending from the bulbous portion 60 in a first direction, and a second wing portion 64 extending from the bulbous portion 60 is a second direction, generally opposite the first direction. Thus the first and second wing portions 62, 64 may extend outwardly in opposing directions from the central bulbous portion 60. In some instances, the balloon 20 may be formed of a non-distensible or stiffer material, such that when the balloon 20 is inflated, the balloon 20 maintains the bulbous portion 60 and wing portions 62, 64 shown in FIG. 3. The winged portions 62, 64 may be configured to follow the curvature of a vessel wall, and thus generally orient the flexible tubular member 40 toward the center of the true lumen of the vessel during use. Furthermore, the bulbous portion 60 may be configured to contact and press against the flexible tubular member 40, thereby deflecting the flexible tubular member 40 upon inflation of the balloon 20.

FIGS. 4 and 5 illustrate an exemplary arrangement of the catheter 10 with the balloon 20 deflated and in a delivery configuration. As shown, the deflated balloon 20 may be folded around the flexible tubular member 40 to provide the distal portion of the catheter 10 with a small delivery profile. For example, in some instances, in the folded delivery configuration, the catheter 10 may have an outer diameter of about 3 French (1 mm) to about 5 French (1.67 mm), for example about 3 French (1 mm), about 3.5 French (1.17 mm), about 4 French (1.33 mm), about 4.5 French (1.5 mm) or about 5 French (1.67 mm). In some embodiments, the distal tip 42 of the flexible tubular member 40 may be wrapped within the folds of the balloon 20 to cover and protect the distal tip 42 from inadvertent contact with the vessel wall during delivery of the balloon 20 and flexible tubular member 40 to a target location in the vasculature. For example, as shown in FIG. 5, portions of balloon material forming the wings 62, 64 may be folded around the flexible tubular member 40 to maintain the flexible tubular member 40 in an elongated configuration generally parallel to the central longitudinal axis of the catheter shaft 12.

Figure 6:
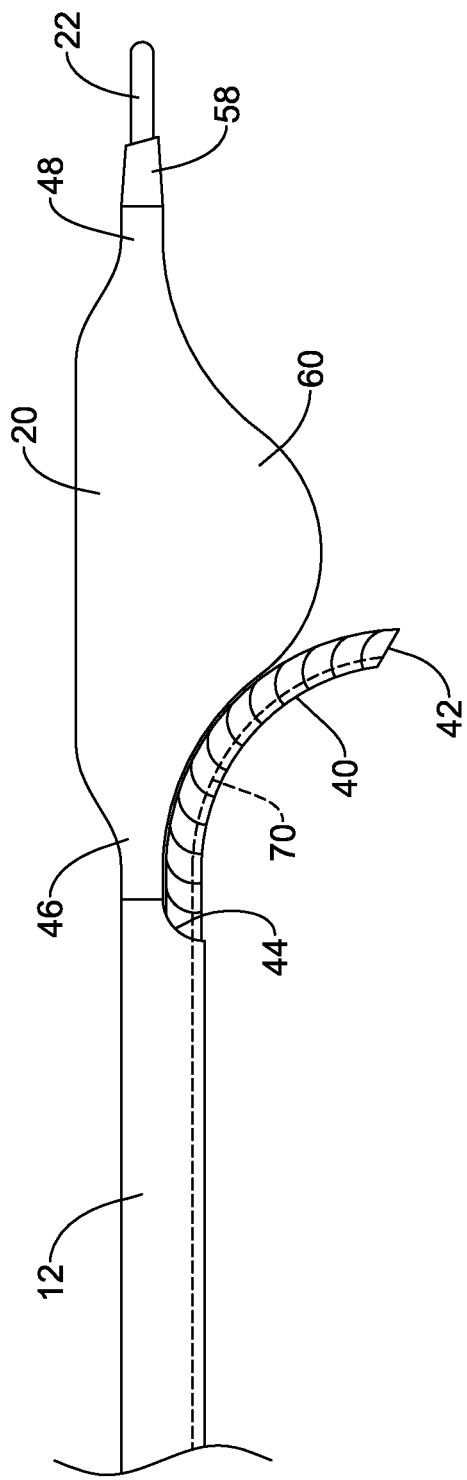
FIG. 6 is a side plan view of an alternative embodiment of the distal portion of the catheter apparatus of FIG. 1 in a deflected configuration.

FIG. 6 illustrates an alternative embodiment, in which the catheter 10 includes a pull wire 70, or other actuation mechanism to facilitate deflecting the flexible tubular member 40 into a curved configuration. For example, the pull wire 70 may have a distal end secured to a distal portion of the flexible tubular member 40 proximate the distal tip 42 of the flexible tubular member 40. Accordingly, the pull wire 70 may extend to the proximal end of the catheter 10, or be attached to an actuatable component accessible at the proximal end of the catheter 10, to be manipulated by the operator to deflect the flexible tubular member 40 into a curved configuration.

Figure 7:
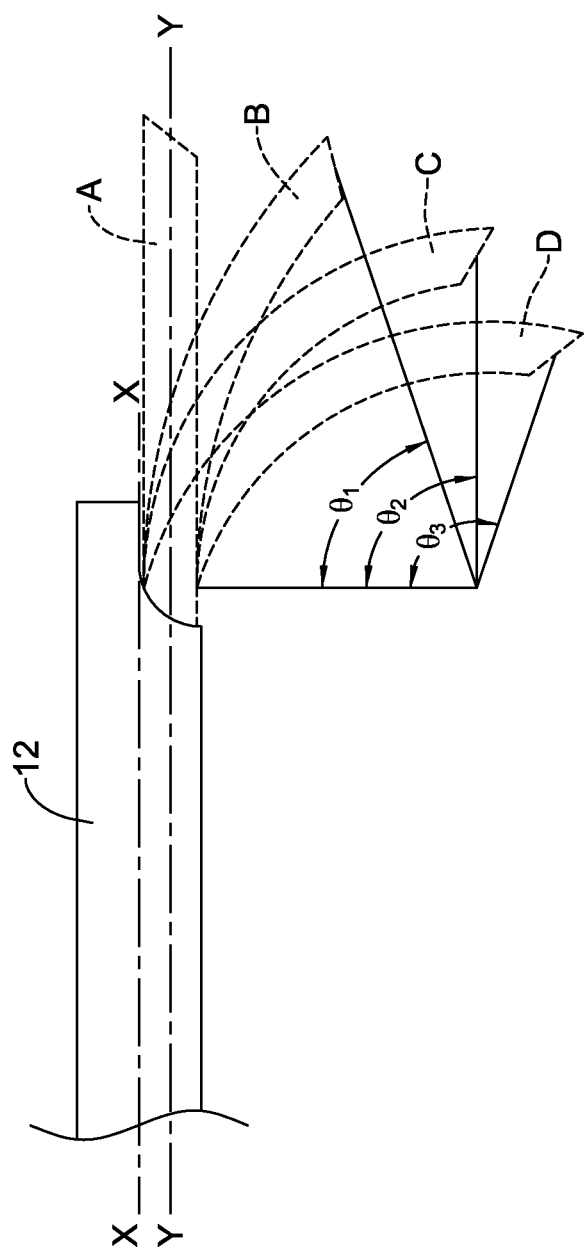
FIG. 7 illustrates possible curved or deflected configurations of the distal portion of the catheter apparatus for re-entry into a true lumen of a blood vessel.

As shown in FIG. 7, the flexible tubular member 40 may be configured to be curved or deflected from a generally axially aligned configuration A in which the flexible tubular member 40 extends along a central longitudinal axis Y generally parallel to the central longitudinal axis X of the main catheter shaft 12 to a curved configuration in which the distal portion of the flexible tubular member 40 is curved away from the longitudinal axis Y. For example, in some embodiments, the distal portion of the flexible tubular member 40 may be curved or deflected to a curved configuration B having an angle of curvature (i.e., arc angle) $\theta_1$ of less than 90°, for example about 30°, about 45°, or about 60°, in some instances. In other embodiments, the distal portion of the flexible tubular member 40 may be curved or deflected to a curved configuration C having an angle of curvature (i.e., arc angle) $\theta_2$ of about 90°. In still other embodiments, the distal portion of the flexible tubular member 40 may be curved or deflected to a curved configuration D having an angle of curvature (i.e., arc angle) $\theta_3$ of greater than 90°, for example about 95° or more, about 100° or more, or about 105° or more in some instances. As described herein, the "arc angle" or "angle of curvature" is intended to be the angle through which the distal portion of the flexible tubular member 40 curves through from the point along the longitudinal axis Y in which the flexible tubular member 40 begins to curve away from the longitudinal axis Y to the center of the opening at the distal tip 42 of the flexible tubular member 40.

In some embodiments, such as embodiments in which the distal tip 42 includes a tapered or sharpened tip, the opening of the lumen 38 at the distal tip 42 may face in a proximal direction in the curved configuration. For instance, the opening of the lumen 38 at the distal tip 42 may face in a proximal direction when the distal portion of the flexible tubular member 40 is deflected through an arc angle of 90° or more, 95° degrees or more, 100° degrees or more, or 105° degrees or more. Accordingly, in such an embodiment, an elongate medical device advanced out of the distal opening of the lumen 38 of the flexible tubular member 40 may be directed in a proximal or retrograde direction, for example.

Figure 8:
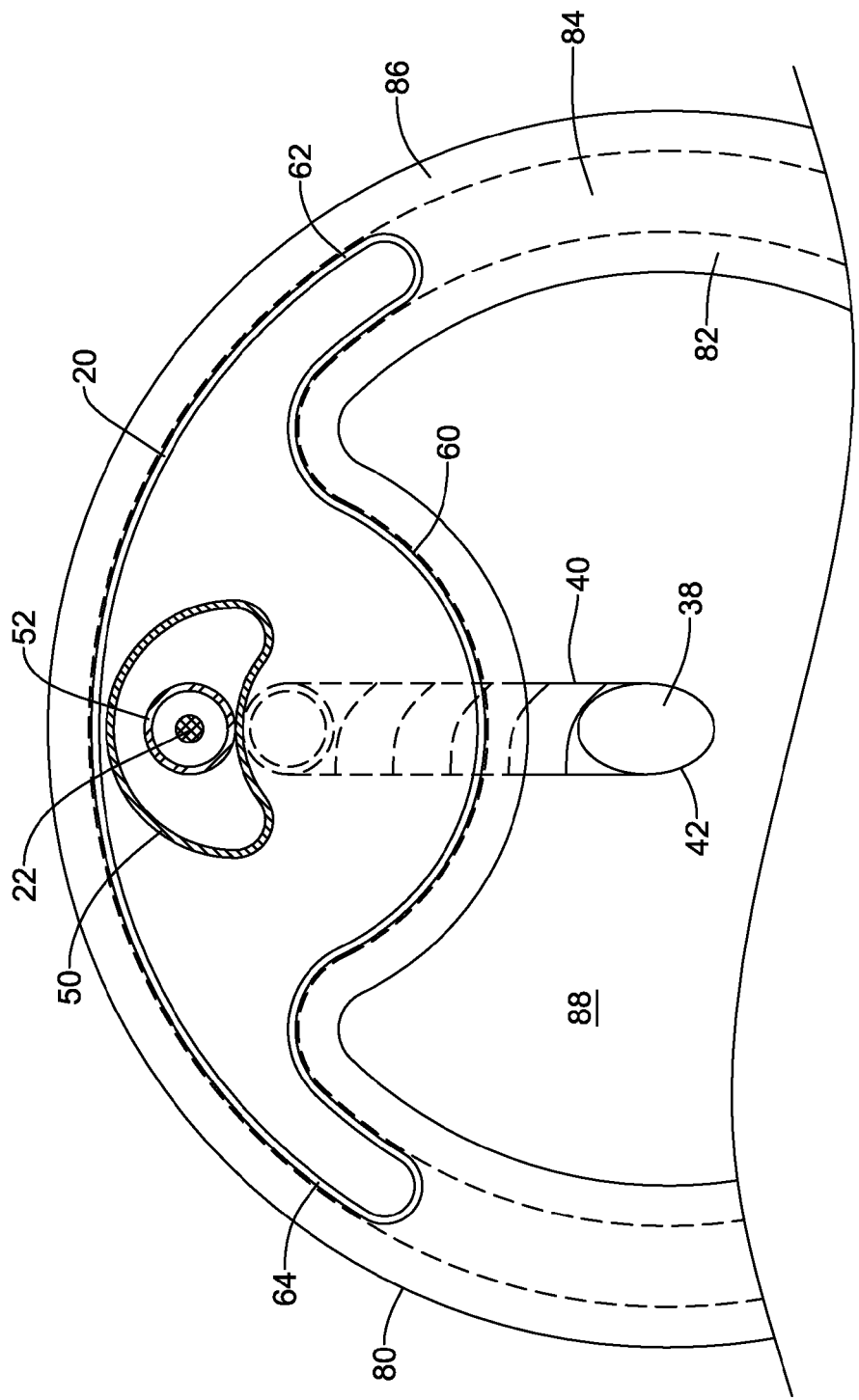
FIG. 8 is a cross-sectional view of the catheter apparatus positioned in the subintimal space of a blood vessel.

FIG. 8 is a cross-sectional view of the distal portion of the catheter 10 positioned in a subintimal space created between two tissue layers of a vessel wall 80. The blood vessel 80 typically has three tissue layers, an innermost layer or intima layer (i.e., tunica intima) 82, an intermediate layer or media layer (i.e., tunica media) 84, and an outermost layer or adventitia layer (tunica adventitia) 86, with the media layer 84 positioned between the intima layer 80 and the adventitia layer 86. The intima layer 82 is a layer of endothelial cells lining the lumen 88 of the vessel 80, as well as a subendothelial layer made up of mostly loose connective tissue. The media layer 84 is a muscular layer formed primarily of circumferentially arranged smooth muscle cells. The adventitia layer 86, which forms the exterior layer of the vessel wall 80 is formed primarily of loose connective tissue made up of fibroblasts and associated collagen fibers.

As will be described further herein, the distal portion of the catheter 10, including the balloon 20, may be advanced into a subintimal space (i.e., a space between the intima layer 82 and the adventitia layer 86) created in the vessel wall 80, such as through dissection of the tissue layers of the vessel wall 80. Once positioned in the subintimal space, the balloon 20 may be inflated between the intima layer 82 and the adventitia layer 86 of the vessel wall 80. As the balloon 20 is inflated, the wings 62, 64 of the balloon 20 may be unfolded and inflated between the intima layer 82 and the adventitia layer 86 to orient the flexible tubular member 40 radially inward of the bulbous portion 60 of the balloon 20. Furthermore, the bulbous portion 60 of the balloon 20 may be inflated to press against the flexible tubular member 40 to deflect the flexible tubular member 40 toward the true lumen 88 of the vessel 80. Inflation of the bulbous portion 60 against the flexible tubular member 40 may cause the distal tip 42 of the flexible tubular member 40 to pierce through the intima layer 82 into the true lumen 88 to allow re-entry into the true lumen 88 with an elongate medical device advanced through the lumen 38. Because the external adventitia layer 86 is more inelastic than the internal intima layer 82, the forces generated through inflation of the balloon 20 may cause the internal intima layer 82 to yield first, bending or folding towards the true lumen 88, rather than causing the external adventitia layer 86 to stretch.

Figure 9:
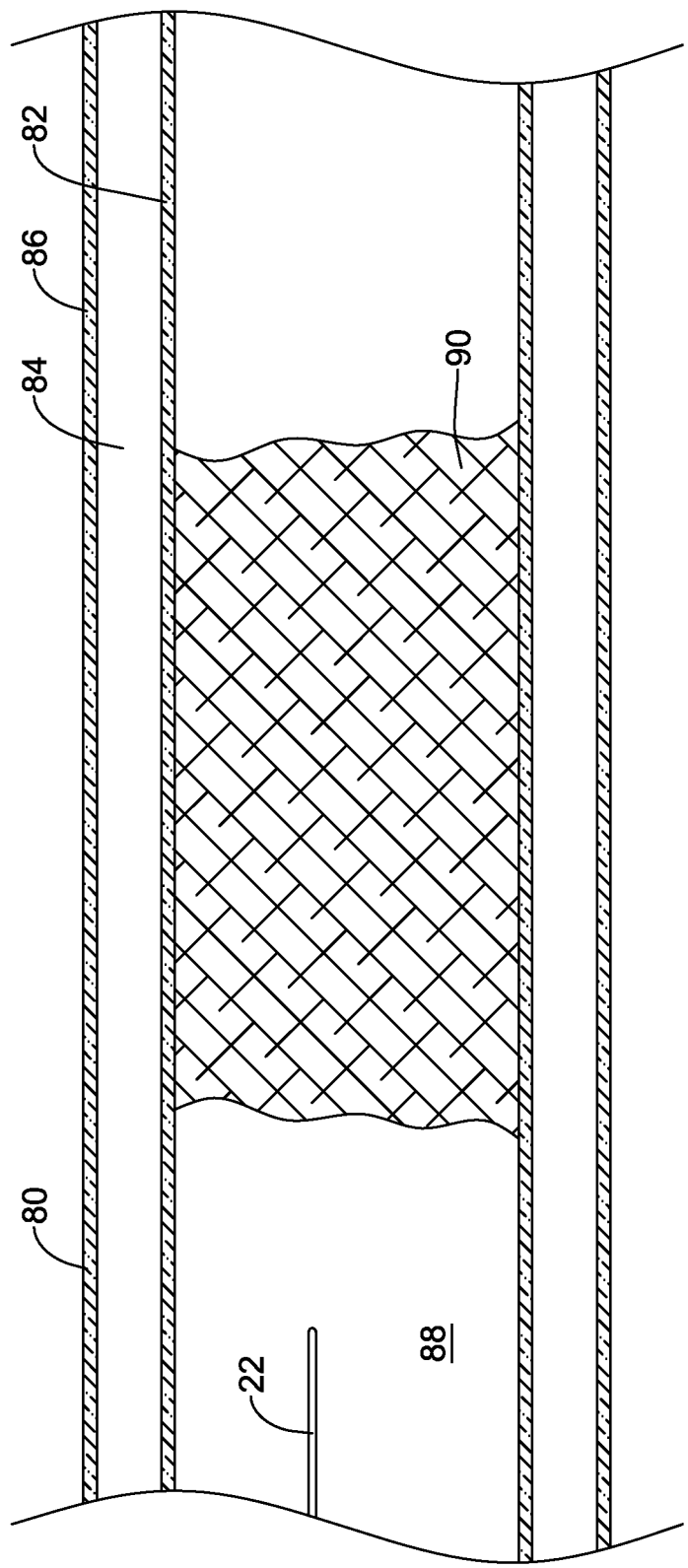
FIGS. 9-14 illustrate aspects of an exemplary method for recanalizing an occluded blood vessel using the catheter apparatus of FIG. 1.
Figure 10:
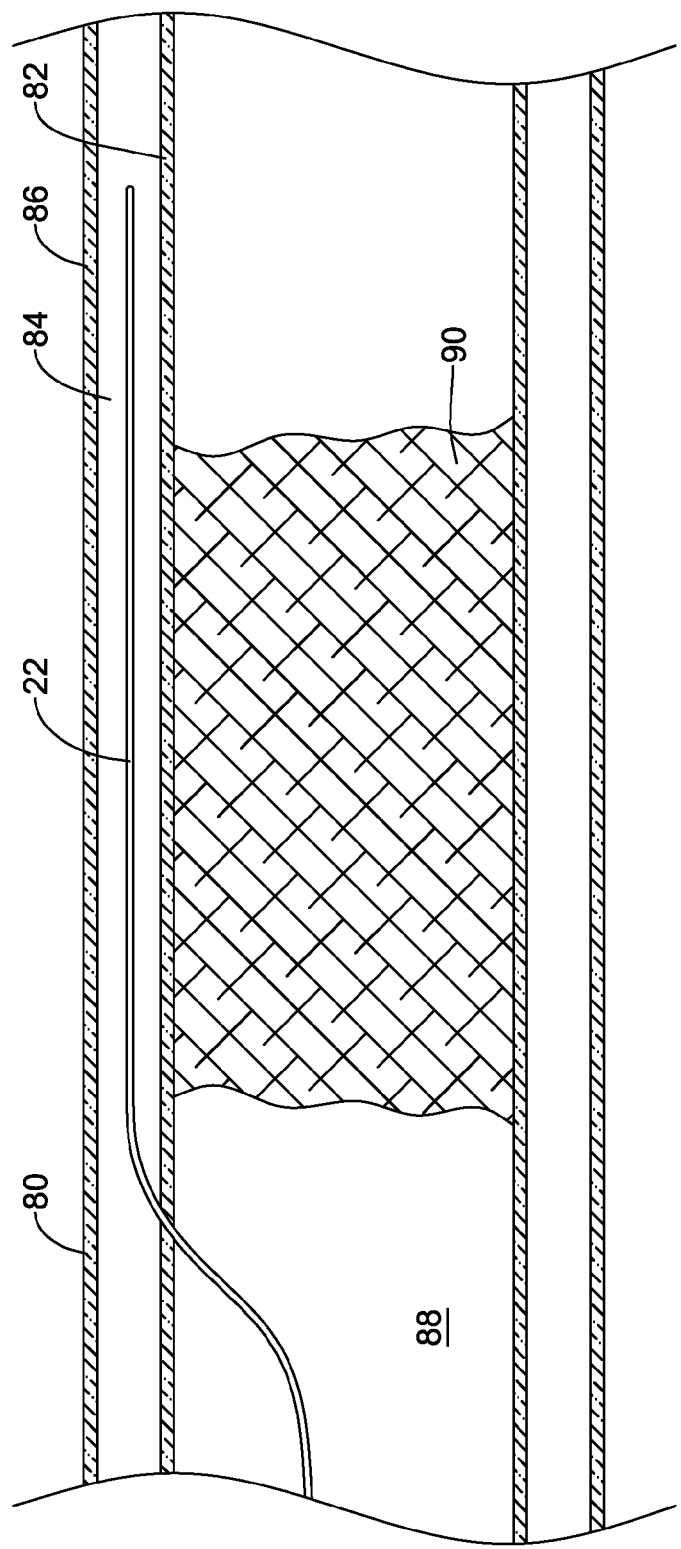

In some instances, it may be undesired, difficult or impossible to pass through an occlusion, such as a chronic total occlusion (CTO) in a lumen of a blood vessel with a medical device to recanalize the vessel. In such instances, it may be possible to recanalize the blood vessel through a subintimal approach using the catheter 10. Turning to FIGS. 9-14, several aspects of an exemplary method for recanalizing an occluded blood vessel using the catheter 10 are illustrated. As shown in FIG. 9, a guidewire 22 may initially be advanced through the lumen 88 of the vessel 80 to a location proximate a proximal end of an occlusion 90 blocking the lumen 88. The guidewire 22 may then be advanced to penetrate outward through the intima layer 82 at a location proximal of the proximal end of the occlusion 90 into the vessel wall 80. With the tip of the guidewire 22 located between the intima layer 82 and the adventitia layer 86, the guidewire 22 may be further advanced distally in a subintimal manner to create a subintimal space between the intima layer 82 and the adventitia layer 86. As shown in FIG. 10, the guidewire 22 may be advanced in a subintimal manner until the distal tip of the guidewire 22 is located distal of the distal end of the occlusion 90 in the subintimal space created, such as by dissection of the tissue layers of the vessel wall 80.

Figure 11:
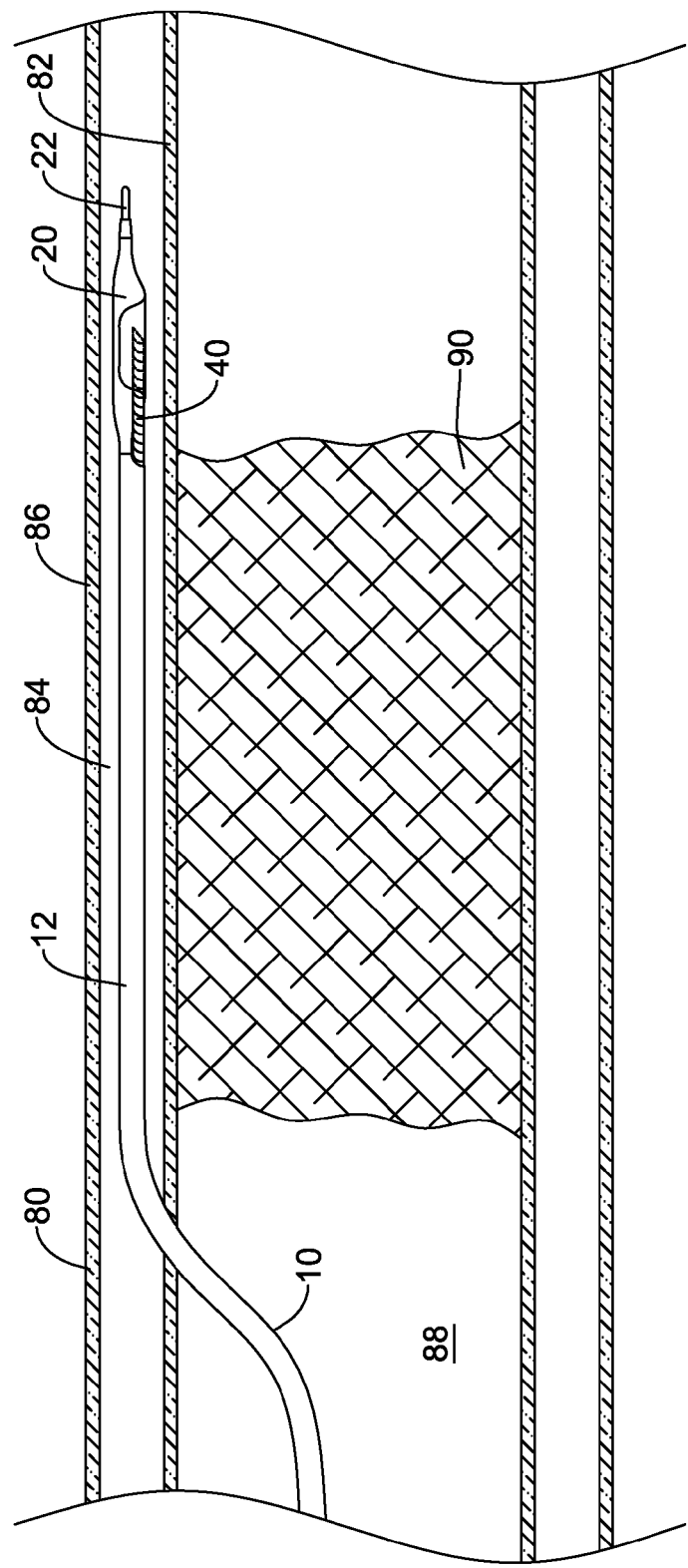

The recanalization catheter 10 may then be advanced distally over the guidewire 22 from the true lumen 88 proximal of the occlusion 90, into the subintimal space between the intima layer 82 and the adventitia layer 86, to a position in the subintimal space in which the distal portion of the catheter 10, including the balloon 20, is located distal of the distal end of the occlusion 90, as shown in FIG. 11. The recanalization catheter 10 may be advanced through the subintimal space in a delivery configuration, such as with the balloon 20 in a deflated, folded configuration wrapped around the flexible tubular member 40 extending from the main catheter shaft 12. In some instances in which the distal tip 58 of the catheter 10 is configured to facilitate piercing and/or dissection of tissue layers of the blood vessel, the sharp, rigid or piercing feature of the distal tip 58 may be used to pierce and/or dissect tissue layers of the vessel wall 80 as the catheter 10 is advanced distally.

Figure 12:
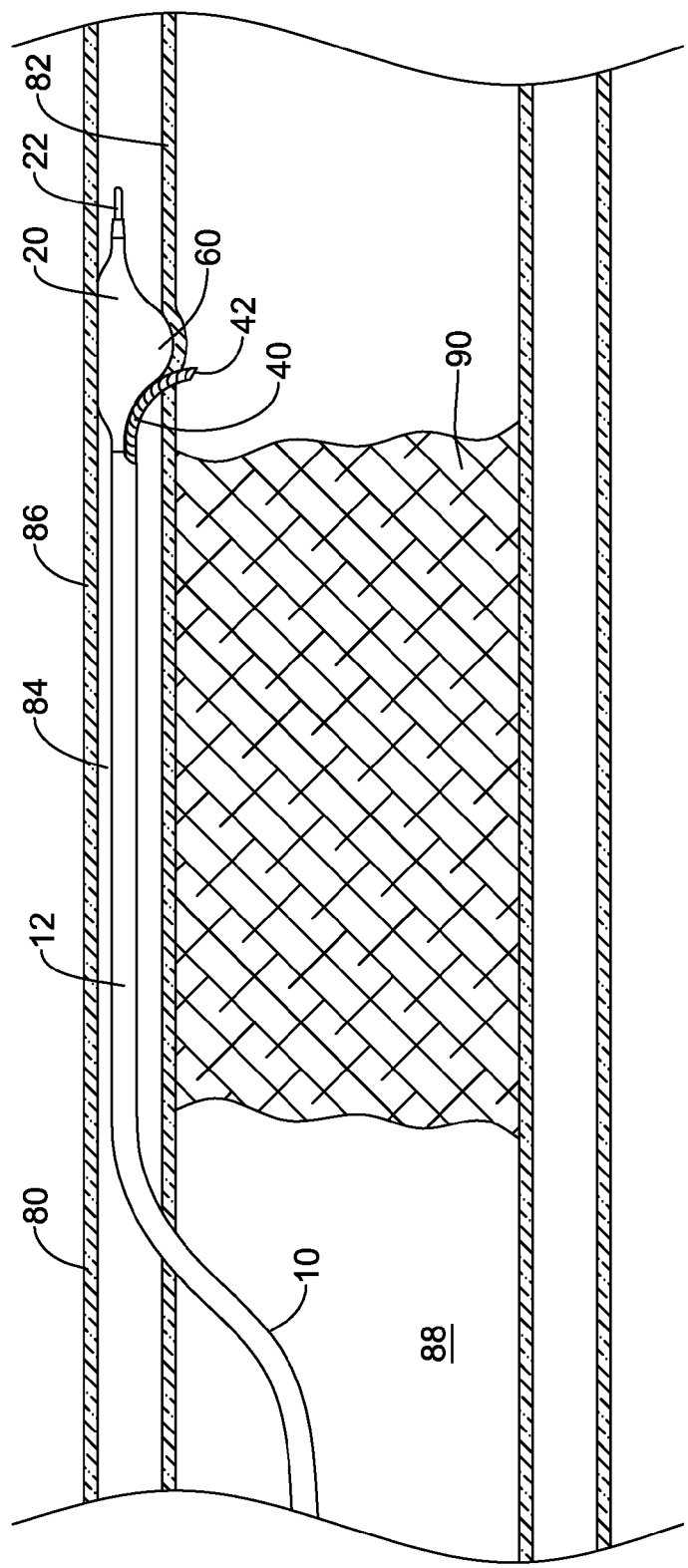

With the balloon 20 positioned distal of the distal end of the occlusion 90, the balloon 20 may be inflated in the subintimal space formed between the intima layer 82 and the adventitia layer 86, as shown in FIG. 12. As the balloon 20 is inflated, the wings 62, 64 of the balloon 20 may be unfolded and inflated between the intima layer 82 and the adventitia layer 86 to orient the flexible tubular member 40 radially inward of the bulbous portion 60 of the balloon 20. Furthermore, the bulbous portion 60 of the balloon 20 may be inflated to press against the flexible tubular member 40 to deflect the flexible tubular member 40 toward the true lumen 88 of the vessel 80. Inflation of the bulbous portion 60 against the flexible tubular member 40 may cause the distal tip 42 of the flexible tubular member 40 to pierce through the intima layer 82 and thus re-enter into the true lumen 88 to allow re-entry into the true lumen 88 distal of the occlusion 90 with an elongate medical device advanced through the lumen 38. In some instances, the pull wire 70 may be actuated to facilitate and/or augment curving the flexible tubular member 40 into a curved configuration. The distal portion of the main catheter shaft 12, including the distal tip of the main catheter shaft 12 and the balloon 20, as well as the guidewire 22, may remain positioned in the subintimal space after the flexible tubular member 40 is deflected into the curved configuration and penetrates into the true lumen 88.

As described above, the flexible tubular member 40 may be configured to be curved or deflected from a generally axially aligned configuration in which the flexible tubular member 40 extends parallel to the main catheter shaft 12 to a curved configuration in which the distal portion of the flexible tubular member 40 is curved away from the longitudinal axis of the main catheter shaft 12. For example, in some embodiments, as shown in FIG. 12, the distal portion of the flexible tubular member 40 may be curved or deflected to a curved configuration having an angle of curvature (i.e., arc angle) of about 90° or greater than 90°, for example about 95° or more, about 100° or more, or about 105° or more in some instances.

Figure 13:
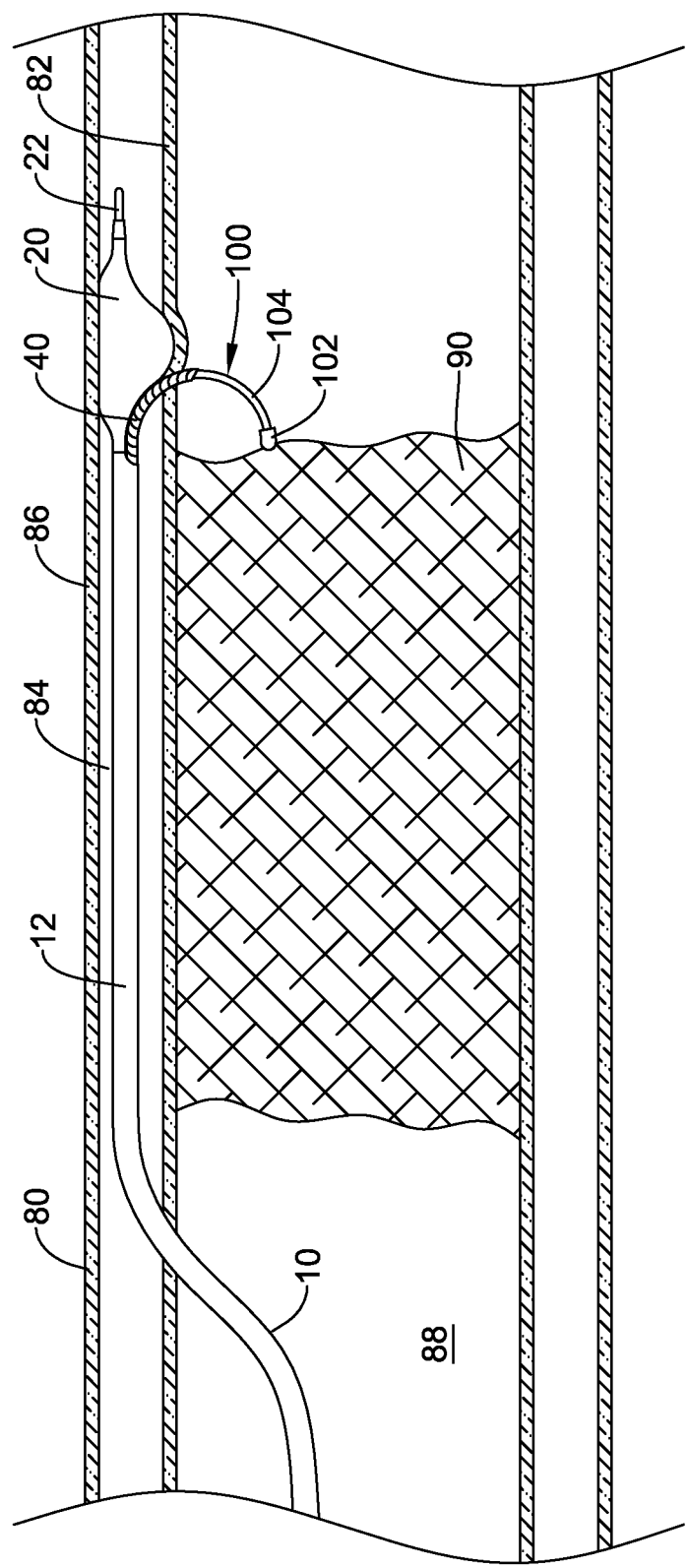

An elongate medical device 100 may then be advanced through the device delivery lumen 38 of the catheter 10 and exit the flexible tubular member 40 into the true lumen 88 distal of the occlusion 90 through the opening in the distal tip 42 of the flexible tubular member 40, shown in FIG. 13. In the embodiment shown in FIG. 13, the flexible tubular member 40 may be curved such that the distal opening of the lumen 38 at the distal tip 42 of the flexible tubular member 40 faces in a proximal direction, and thus faces the distal end of the occlusion 90. Accordingly, the elongate medical device 100, upon exiting the flexible tubular member 40, may be directed or advanced proximally toward the distal end of the occlusion 90. In instances in which the elongate medical device 100 is an occlusion crossing device, such as an atherectomy device, a needle-tipped catheter, a stylet or a guidewire, the elongate medical device may be directed or advanced proximally from the distal opening of the lumen 38 of the flexible tubular member 40 toward the distal end of the occlusion 90 to penetrate into or through the occlusion 90 in a retrograde manner.

As shown in FIG. 13, in some instances the elongate medical device 100 may be an atherectomy device having an elongate shaft 104 with a distal cutting tip 102 attached thereto for penetrating into or through the occlusion 90. For example, in some instances, the distal cutting tip 102 may be a rotatable cutting tip or burr, such as a micro burr, expandable burr, an angled burr, an enhanced wire tip burr, a diamond coated burr, or other cutting device. In other instances, the distal cutting tip 102 may be an ablation electrode or ultrasound transducer configured for ablating a pathway through the occlusion 90.

Figure 14:
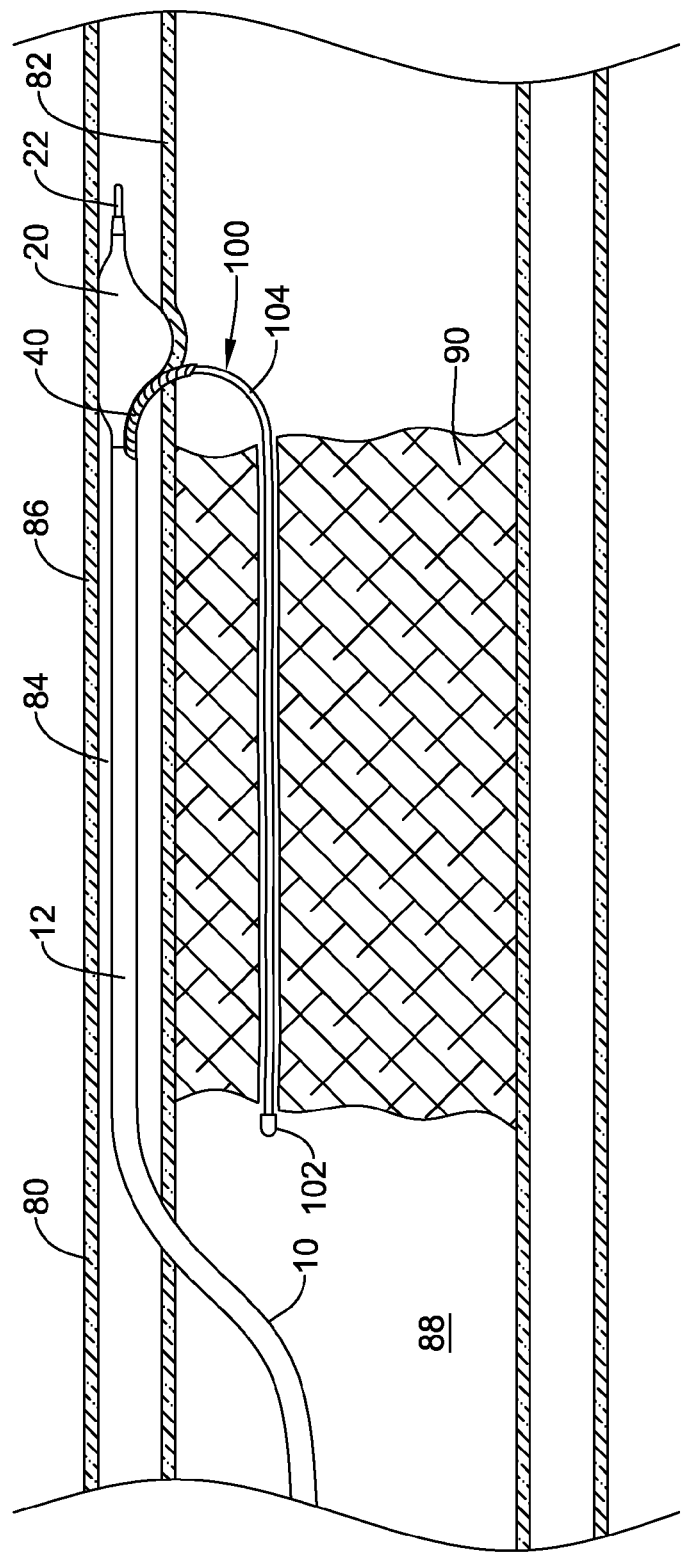

From the re-entry location distal of the occlusion 90, the elongate medical device 100 (e.g., occlusion crossing device) may be advanced in a retrograde direction (i.e., proximally) into the distal end of the occlusion 90. In such a fashion, the elongate medical device 100 may be advanced through the occlusion 90 from the distal end of the occlusion 90 to the proximal end of the occlusion 90 in a retrograde manner, as shown in FIG. 14, to create a pathway through the occlusion 90 to recanalize the vessel and provide a pathway through the occlusion 90 for blood to flow therethrough.

In a retrograde approach of crossing the occlusion 90 in such a manner, there may be less concern with the fluid flow and circumstances associated therewith. For example, emboli created while boring or ablating through the occlusion 90 may flow distally away from the occlusion 90 as the atherectomy device is advanced through the occlusion 90.

Figure 15:
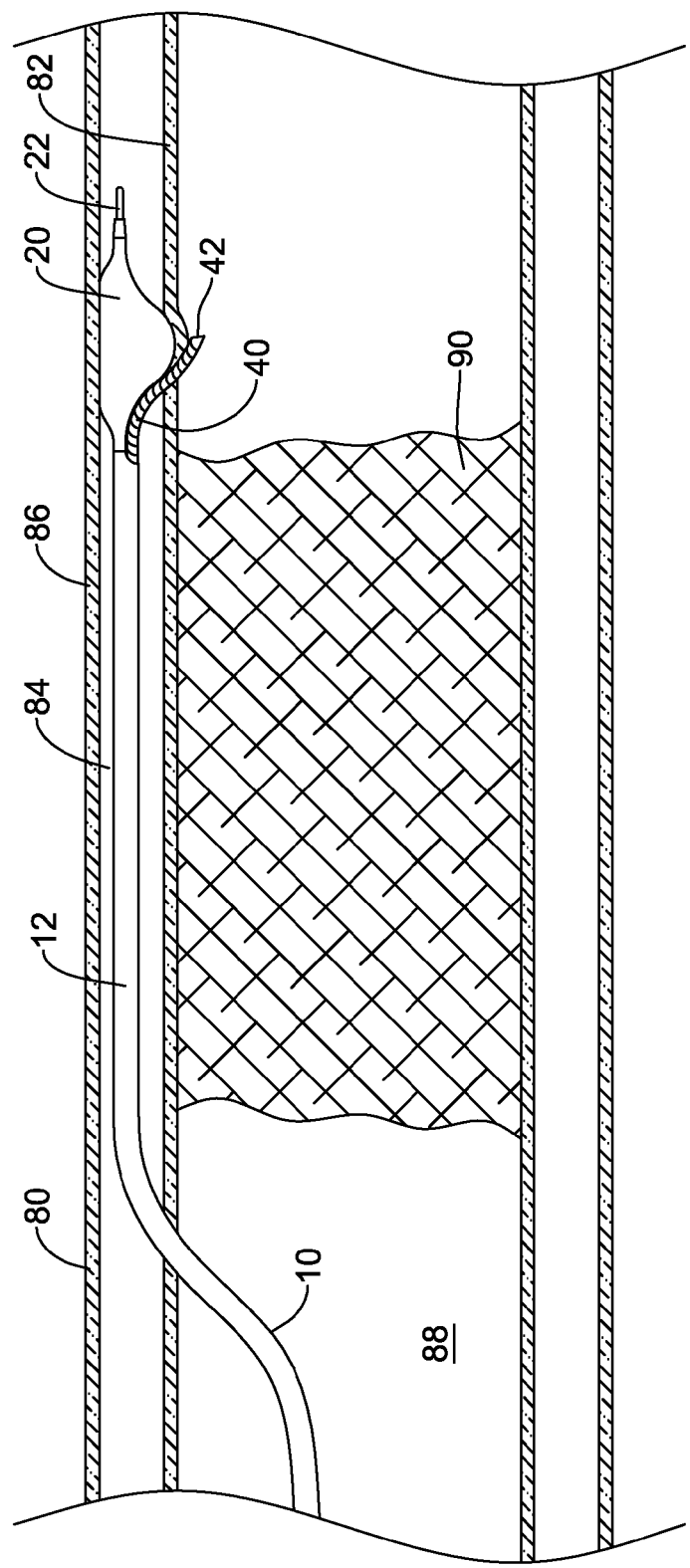
FIGS. 15-16 illustrate aspects of another exemplary method for recanalizing an occluded blood vessel using the catheter apparatus of FIG. 1.

In other embodiments, such as shown in FIG. 15, the balloon 20 may be inflated in the subintimal space formed between the intima layer 82 and the adventitia layer 86 to deflect the flexible tubular member 40 into a curved configuration by inflating the bulbous portion 60 of the balloon 20 against the flexible tubular member 40 to deflect the flexible tubular member 40 toward the true lumen 88 of the vessel 80. Inflation of the bulbous portion 60 against the flexible tubular member 40 may cause the distal tip 42 of the flexible tubular member 40 to pierce through the intima layer 82 and thus re-enter into the true lumen 88 to allow re-entry into the true lumen 88 distal of the occlusion 90 with an elongate medical device advanced through the lumen 38. In some instances, the pull wire 70 may be actuated to facilitate and/or augment curving the flexible tubular member 40 into a curved configuration. The distal portion of the main catheter shaft 12, including the distal tip of the main catheter shaft 12 and the balloon 20, as well as the guidewire 22, may remain positioned in the subintimal space after the flexible tubular member 40 is deflected into the curved configuration and penetrates into the true lumen 88.

Alternatively, inflation of the bulbous portion 60 against the flexible tubular member 40 may cause the distal tip 42 of the flexible tubular member 40 to be oriented toward the intima layer 82 and an elongate medical device, such as a guidewire, a stylet, a needle, or other device may be advanced through the flexible tubular member 40 to pierce through the intima layer 82 to re-enter into the true lumen 88 distal of the occlusion 90.

As described above, the flexible tubular member 40 may be configured to be curved or deflected from a generally axially aligned configuration in which the flexible tubular member 40 extends parallel to the main catheter shaft 12 to a curved configuration in which the distal portion of the flexible tubular member 40 is curved away from the longitudinal axis of the main catheter shaft 12. For example, as shown in FIG. 15, the distal portion of the flexible tubular member 40 may be curved or deflected to a curved configuration having an angle of curvature (i.e., arc angle) of less than 90° such that the distal opening of the lumen 38 at the distal tip 42 of the flexible tubular member 40 faces in a distal direction.

Figure 16:
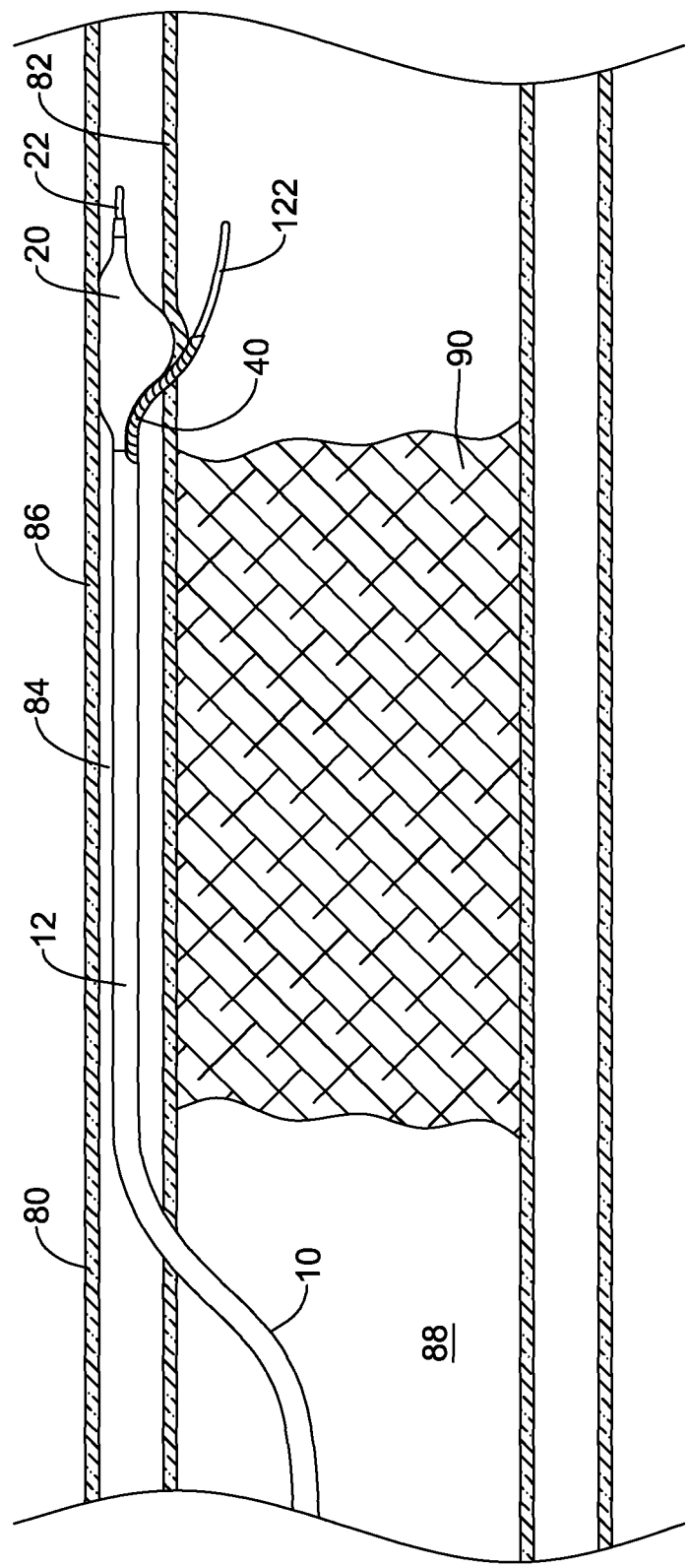

An elongate medical device 100 may then be advanced through the device delivery lumen 38 of the catheter 10 and exit the flexible tubular member 40 into the true lumen 88 distal of the occlusion 90 through the opening in the distal tip 42 of the flexible tubular member 40, shown in FIG. 16. In the embodiment shown in FIG. 16, the flexible tubular member 40 may be curved such that the distal opening of the lumen 38 at the distal tip 42 of the flexible tubular member 40 faces in a distal direction, and thus faces away from the distal end of the occlusion 90. Accordingly, the elongate medical device 100, upon exiting the flexible tubular member 40, may be directed or advanced distally through the true lumen 88 away from the distal end of the occlusion 90.

Once a pathway has been created across the occlusion 90, either through the occlusion 90 and/or around the occlusion 90 via a subintimal track, one or more additional medical devices may be advanced through the blood vessel 80 to enlarge the pathway and/or pass distally of the occlusion 90 to perform a further medical procedure.

Those skilled in the art will recognize that aspects of the present disclosure may be manifested in a variety of forms other than the specific embodiments described and contemplated herein. Accordingly, departure in form and detail may be made without departing from the scope and spirit of the present disclosure as described in the appended claims.

What is claimed is:

1. A catheter for recanalizing a blood vessel having an occlusion therein, the catheter comprising:
 a catheter shaft having a longitudinal axis, a proximal end, a distal end, and a distal end portion proximate the distal end;
 an expandable member coupled to the distal end portion of the catheter shaft, wherein the expandable member includes an inflatable first wing portion and an inflatable second wing portion, each of the first and second wing portions extending laterally away from the longitudinal axis on opposing sides of the longitudinal axis; and
 a flexible tubular member extending from the catheter shaft and along an exterior of the expandable member;
 wherein expansion of the expandable member deflects the flexible tubular member into a deflected configuration away from a longitudinal axis of the catheter shaft.

2. The catheter of claim 1, wherein in a delivery configuration the flexible tubular member has a central longitudinal axis generally parallel to the longitudinal axis of the catheter shaft.

3. The catheter of claim 2, wherein the expandable member is an inflatable balloon secured to the distal end portion of the catheter shaft.

4. The catheter of claim 3, wherein inflation of the balloon curves the flexible tubular member away from the catheter shaft in the deflected configuration.

5. The catheter of claim 4, wherein the flexible tubular member includes a distal opening at a distal end of the tubular member, wherein the distal opening faces proximally in the deflected configuration.

6. The catheter of claim 1, wherein the expandable member is an inflatable balloon including a bulbous portion located between the first wing portion and the second wing portion.

7. The catheter of claim 6, wherein the bulbous portion of the inflatable balloon is configured to be inflated against the flexible tubular member to deflect the flexible tubular member into a curved configuration.

8. The catheter of claim 1, wherein the flexible tubular member is a metallic tubular member having a helical slit extending therethrough.

9. The catheter of claim 8, wherein the metallic tubular member has an angled tip.

10. A catheter assembly for navigating through a lumen of a blood vessel to an occlusion in an antegrade direction that is configured to redirect an atherectomy device toward the occlusion in a retrograde direction in the lumen of the blood vessel, the catheter assembly comprising:
 a catheter shaft having a longitudinal axis, a proximal end, a distal end and a distal end portion proximate the distal end;
 an inflatable balloon secured to the distal end portion of the catheter shaft, wherein the balloon includes an inflatable first wing portion and an inflatable second wing portion, each of the first and second inflatable wing portions extending laterally away from the longitudinal axis on opposing sides of the longitudinal axis; and
 a tubular member extending distally from a location on the catheter shaft proximal of the inflatable balloon, the tubular member configured to be deflectable away from the catheter shaft into a curved configuration upon inflation of the inflatable balloon.

11. The catheter assembly of claim 10, wherein the tubular member extends along an exterior of the inflatable balloon.

12. The catheter assembly of claim 10, wherein the tubular member defines an atherectomy lumen configured to slidably receive an atherectomy device therein.

13. The catheter assembly of claim 12, further comprising an atherectomy device extendable through the atherectomy lumen.

14. The catheter assembly of claim 10, wherein the tubular member curves through at least 90 degrees in the curved configuration.

15. The catheter assembly of claim 10, wherein the tubular member curves through at least 100 degrees in the curved configuration.

16. The catheter assembly of claim 10, wherein the tubular member includes a distal opening configured to face in a proximal direction in the curved configuration.

* * * * *